(12) United States Patent
Kent et al.

(10) Patent No.: US 6,642,357 B1
(45) Date of Patent: *Nov. 4, 2003

(54) PROCESS FOR PREPARING MODIFIED PROTEINS

(75) Inventors: Stephen B. H. Kent, La Jolla, CA (US); Martina Schnolzer-Rackwitz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/222,625

(22) Filed: Dec. 29, 1998

Related U.S. Application Data

(62) Division of application No. 08/312,662, filed on Sep. 26, 1994, now Pat. No. 5,854,389, which is a continuation of application No. 07/865,368, filed on Apr. 7, 1992, now abandoned.

(51) Int. Cl.$^7$ .............................................. C07K 14/00
(52) U.S. Cl. ....................... 530/332; 530/323; 530/324; 530/345; 514/12
(58) Field of Search ................................ 530/332, 328, 530/329, 330, 323, 345; 514/12

(56) References Cited

U.S. PATENT DOCUMENTS

| | | | |
|---|---|---|---|
| 4,596,675 A | * 6/1986 | Weingarten | 530/323 |
| 4,946,839 A | 8/1990 | Kozikowskip et al. | 514/210 |
| 4,990,504 A | 2/1991 | Kozikowski et al. | 514/210 |
| 5,066,716 A | * 11/1991 | Robey | 525/54.1 |
| 5,286,846 A | 2/1994 | Inman et al. | 530/300 |
| 5,371,197 A | 12/1994 | Marburg et al. | 530/404 |
| 5,387,671 A | * 2/1995 | Kawai | 530/329 |
| 5,453,269 A | 9/1995 | Haber et al. | 424/136.1 |
| 5,484,722 A | 1/1996 | Friesen et al. | 435/188 |
| 5,831,005 A | * 11/1998 | Zuckerman | 530/333 |
| 5,891,993 A | * 4/1999 | Dawson | 530/323 |

FOREIGN PATENT DOCUMENTS

| | | |
|---|---|---|
| EP | 0 210 628 | 3/1983 |
| WO | 8801173 | 9/1986 |
| WO | 9212168 | 12/1990 |

OTHER PUBLICATIONS

McRae, Biochemistry 20, 7196, 1981.*
Armstrong, Biochem J. 248 703, 1987.*
Sottrup–Jensen, Proc. Natl. Acad. Sci 82, 9, 1985.*
Lipman, Biochemistry 9, 4846–4851, 1970.*
Sasaki, et al., "Helichrome: Synthesis and Enzymatic Activity of a Designed Hemeprotein",*J. Am. Chem. Soc.* 111:380–381 (1989).
Mutter, et al., "The Construction of New Proteins: V. A Template–Assembled Synthetic Protein (TASP) Containing Both a 4–Helix Bundle and β–Barrel–Like Structure", *Proteins: Structure, Function, and Genetics* 5: 13–21 (1989).

Mutter, et al., "A Chemical Approach to Protein Design–Template–Assembled Synthetic Proteins (TASP)", *Ang. Chem. Int. Ed. Eng. 28*: 535–554 (1989).
Robey, et al., "Automated Synthesis of N–Bromoacetyl–M-odified Peptides for the Preparation of Synthetic Peptide Polymers, Peptide–Protein Conjugates, and Cyclic Peptides", *Anal. Biochem. 177*: 373–377 (1989).
Ernest, et al., "Synthesis of a 4–Helix Bundle–Like Template–Assembled Synthetic Protein (TASP) by Condensation of a Protected Peptide on a Conformationally Constrained Cyclic Carrier", *Tetrahedron Lett. 31*: 4015–4018 (1990).
Mutter, et al., "Template–Assembled Synthetic Proteins with Four–Helix–Bundle Topology. Total Chemical Synthesis and Conformational Studies", *J. Am. Chem. Soc. 114*: 1463–1470 (1992).
Degrado, et al., "Protein Design, a Minimalist Approach", *Science 243*: 622–628 (1989).
Ellman, et al., "Site–Specific Incorporation of Novel Backbone Structures into Proteins", *Science 255*: 197–200 (1992).
Noren, et al., "A General Method for Site–Specific Incorporation of Unnatural Amino Acids into Proteins", *Science 244*: 182–188 (1989).
Kohl, et al., "Active Human Immunodeficiency Virus Protease is Required for Viral Infectivity", *Proc. Natl. Acad. Sci. USA 85*: 4686–4690 (1988).
Mascagni, et al., "Protein Engineering of HIV Viral Proteins by Total Chemical Synthesis: The C–Terminal 104 Residue Peptide from GAG p24", *Tetrahedron Lett. 31*: 4637–4640 (1990).
Beattie, et al., "Solid–Phase Gene Assembly", *Nature 352*: 458–459 (1991).
McRae, et al., "Mapping the Active Sites of Bovine Thrombin, Factor Ixa, Factor Xa, Factor Xia, Factor XIIa, Plasma Kallikrein, and Trypsin with Amino Acid and Peptide Thioesters: Development of New Sensitive Substrates", *Biochemistry 20*: 7196–7206 (1981).
Mutter, et al., "Strategies for the De Novo Design of Proteins", *Tetrahedron 44*: 771–785 (1988).
Rose, et al., "Preparation of Well–Defined Protein Conjugates Using Enzyme–Assisted Reverse Proteolysis", *Bioconjugate Chem. 2*: 154–159 (1991).
Roskoski, et al., "Isolation of Enzyme–Bound Peptide Intermediates in Tyrocidine Biosynthesis", *Biochemistry 9*: 4846–4851 (1970).

(List continued on next page.)

Primary Examiner—Christopher S. F. Low
Assistant Examiner—David Lukton
(74) *Attorney, Agent, or Firm*—Donald G. Lewis

(57) ABSTRACT

Modified proteins are represented by the formula R-L-R', wherein R and R' are peptides or pseudopeptides linked to one another by linkage L. Linkage L may be either a thiol ester pseudopeptide backbone linkage or a selenol ester pseudopeptide backbone linkage.

7 Claims, 6 Drawing Sheets

OTHER PUBLICATIONS

Spatola, et al., "Synthesis and Biological Activities of Pseudopeptide Analogues of LH–RH: Agonists and Antagonists", *Biochem. Biophys. Res. Commun.* 97: 1014–1023 (1980).

Sottrup–Jensen, et al., "Common evolutionary origin of $\alpha_2$–macroglobulin and complement components C3 and C4", *Proc. Natl. Acad. Sci. USA* 82: 9–13 (1985).

Offord, "Protein Engineering by Chemical Means?", *Protein Engineering* 1: 151–157 (1987).

Armstrong, et al., "Limulus $\alpha_2$–macroglobulin", *Biochem. J.* 248: 703–707 (1987).

Yamashiro, et al., "New segment synthesis of $\alpha$–inhibin–92 by the acyl disulfide method", *Int. J. Peptide Protein Res.* 31: 322–334 (1988).

Schnölzer, et al., "Constructing Proteins by Dovetailing Unprotected Synthetic Peptides: Backbone–Engineered HIV Protease", *Science* 256: 221–225 (1992).

* cited by examiner

```
                       SEQUENCE LISTING

<160> NUMBER OF SEQ ID NOS: 4

<210> SEQ ID NO 1
<211> LENGTH: 47
<212> TYPE: PRT
<213> ORGANISM: Human immunodeficiency virus type 1

<400> SEQUENCE: 1

Phe Ile Lys Val Arg Gln Tyr Asp Gln Ile Pro Val Glu Ile Cys Gly
 1               5                  10                  15

His Lys Ala Ile Gly Thr Val Leu Val Gly Pro Thr Pro Val Asn Ile
            20                  25                  30

Ile Gly Arg Asn Leu Leu Thr Gln Ile Gly Cys Thr Leu Asn Phe
        35                  40                  45

<210> SEQ ID NO 2
<211> LENGTH: 51
<212> TYPE: PRT
<213> ORGANISM: Human immunodeficiency virus type 1

<400> SEQUENCE: 2

Pro Gln Ile Thr Leu Trp Gln Arg Pro Leu Val Thr Ile Arg Ile Gly
 1               5                  10                  15

Gly Gln Leu Lys Glu Ala Leu Leu Asp Thr Gly Ala Asp Asp Thr Val
            20                  25                  30

Leu Glu Glu Met Asn Leu Pro Gly Lys Trp Lys Pro Lys Met Ile Gly
        35                  40                  45

Gly Ile Gly
    50

<210> SEQ ID NO 3
<211> LENGTH: 6
<212> TYPE: PRT
<213> ORGANISM: Artificial Sequence
<220> FEATURE:
<223> OTHER INFORMATION: synthesized
<221> NAME/KEY: ACETYLATION
<222> LOCATION: (1)...(1)
<221> NAME/KEY: VARIANT
<222> LOCATION: 3-4
<223> OTHER INFORMATION: Xaa is norleucine
<221> NAME/KEY: AMIDATION
<222> LOCATION: (6)...(6)

<400> SEQUENCE: 3

Thr Ile Xaa Xaa Gln Arg
 1               5

<210> SEQ ID NO 4
<211> LENGTH: 6
<212> TYPE: PRT
<213> ORGANISM: Artificial Sequence
<220> FEATURE:
<223> OTHER INFORMATION: synthesized
<221> NAME/KEY: MOD_RES
```

```
<222> LOCATION: (1)...(1)
<223> OTHER INFORMATION: modified with 2-aminobenzoyl
<221> NAME/KEY: VARIANT
<222> LOCATION: 3
<223> OTHER INFORMATION: Xaa is norleucine
<221> NAME/KEY: AMIDATION
<222> LOCATION: (6)...(6)

<400> SEQUENCE: 4

Thr Ile Xaa Phe Gln Arg
  1               5
```

PROCESS FOR PREPARING MODIFIED PROTEINS

This application is a divisional of Ser. No. 08/312,662, filed Sep. 26, 1994, now U.S. Pat. No. 5,854,389, which is a continuation of Ser. No. 07/865,368, filed Apr. 7,1992, now abandoned.

BACKGROUND OF THE INVENTION

1. Field of the Invention

This invention is in the area of modified biomolecules and methods of making such modified biomolecules. More particularly, this invention relates to protein engineering by chemical means to produce modified proteins where one or more peptide bonds are substituted by non-peptide linkage and one or more encoded amino acids may be replaced by unnatural amino acids or amino acid analogs or any other non-coded structure.

2. Related Art

Numerous attempts have been made to develop a successful methodology for synthesizing modified biomolecules such as proteins, glycoproteins, nucleotides, polysaccharides, and other biopolymers. Such modified biomolecules are invaluable for study of structure-activity relationships of native biomolecules and there is a growing number of commercial applications of these molecules for diagnostic or therapeutic purposes.

Structural modification of proteins and peptides, normally referred to as "protein engineering" involves the rationally designed alteration of structure with the aim of understanding protein structure and function and of creating a protein with new desirable properties. In the past, this has been principally carried out by site-directed mutagenesis or other techniques involving genetic manipulation. The major drawbacks of these prior art approaches are that amino acids replacing native amino acids are those that must be coded genetically. As a result, other structural variants such as unnatural amino acids or amino acid analogs cannot be introduced in the protein backbone. However, recent findings (Ellman, et al., *Science*, 255:197, 1992; Noren, et al., *Science*, 24:182, 1989) would allow unnatural amino acids or amino acid analogs to be incorporated into proteins in a site-specific manner. In this approach, a codon encoding an amino acid to be replaced is substituted by the nonsense codon TAG by means of oligonucleotide-directed mutagenesis. A suppressor tRNA directed against this codon is then chemically aminoacylated with the desired unnatural amino acid. Addition of the amino acylated tRNA to an in vitro protein synthesizing system programmed with the mutagenized DNA directs the insertion of the prescribed amino acid into the protein at the target site. Taking the enzyme T4 lysozyme, the above authors, incorporated a wide variety of amino acid analogs into the enzyme at alanine 82 position with a few exceptions, for example, of D-alanine not being incorporated.

While Schultz's approach partially solves problems posed by biosynthetic protein engineering, it does not allow the alteration of the protein backbone at more than one target site to incorporate two or more different non-coded structural units. Also, by the very nature of the system, i.e., the fact that it relies upon a living system to produce the engineered protein, many substitutions or alterations, such as those which would result in a lethal mutation, cannot be done. The chemical synthesis would overcome the shortcomings left by the Schultz techniques. (reviewed by R. E. Offord, *Protein Eng.*, 1:151, 1987). However, chemical synthesis is fraught with many difficulties such as the need of protection of unwanted reactive groups.

Overall, there is a definite need for a simple and efficient method for making a modified protein which posses desired properties. The present invention addresses such need and provides novel modified proteins.

SUMMARY OF THE INVENTION

This invention provides new and useful modified biomolecules. It also provides a new process for producing such modified biomolecules. In general, the modified biomolecules of this invention comprise two molecular segments, each selected from peptides, pseudopeptides, or non-peptide linear molecules linked through a non-amido linkage to form a peptide or pseudopeptide backbone, wherein one or the segment contains at least one non-coded structural unit and the non-coded structural unit does not form a part of the non-amido linkage. The chemical bonding of the two segments is by means of terminal reactive groups on one segment which react with reactive groups of the other segment molecule.

The process of this invention provides a directed ligation of the two molecular segments to create a desired bond at the ligation point(s) and comprises the steps of:

a. providing a first segment having at least one non-coded structural unit and attaching a first chemoselective synthon to the first segment at the terminal position thereof;

b. providing a second segment optionally containing at least one non-coded structural unit, and second chemoselective synthon at the terminal position thereof, the second chemoselective synthon being complementary to the first chemoselective synthon of the first segment; and c. ligating the first segment and the second segment, whereby the first synthon of the first segment and the second synthon of the second segment forms a non-peptide linkage, wherein the first segment and the second segment are each selected from peptides, pseudopeptides, or non-peptide linear molecules, provided that both segments are not non-peptide linear molecules at the same time.

The above sequence a–c can be repeated by using a first modified biomolecule as the first segment to which a second segment or a second biomolecule is ligated. The present process also may include the step of ligating additional segments with the first and second segments which have been provided with additional terminal synthons that are compatible with the first and second synthons and chemoselective to synthons of the additional segments.

The present invention is therefore applicable in the chemical synthesis of various protein conjugates, such as proteins with reporter molecules, radionuclides, cytotoxic agents, nucleotides, antibodies, and non-protein micromolecules.

Preferably, the process of this invention involves a series of steps comprising:

a. sequentially coupling selected amino acids or amino acid analogs to a terminal amino acid or amino acid analog bound to a first resin support to form a first peptide segment-resin, the first peptide segment having about two to about one hundred amino acid residues;

b. covalently attaching a haloacyl moiety to the N-terminus of the first peptide segment-resin to form a haloacylpeptide segment bound to the first resin support;

c. cleaving the haloacylpeptide peptide segment from the first resin support;

d. sequentially coupling selected amino acids or amino acid analogs to a terminal amino acid or amino acid analog bound to a second resin support through a sulfur or selenium-containing bond to form a second peptide segment-resin, the second peptide segment having about two to about one hundred amino acid residues;

e. cleaving the second peptide segment-resin to form a second peptide segment having a thiol- or selenol- containing group at the C-terminus thereof; and f. coupling the haloacylpeptide peptide segment and the second peptide segment to form a modified polypeptide.

The order of the sequence of steps a-b-c-d-e- is not critical to this invention. The sequence of steps a-b-c and the sequence of steps d may be conducted successively or separately. The entire sequence can be repeated in a chain-reaction manner.

Optionally, any reactive groups such as thiol that may be present in the peptide segments can be protected prior to step (f) and deprotected after step (f) is complete.

This invention, in its broadest sense, encompasses a biologically active protein comprising two molecular segments, each selected from peptides, pseudopeptides, or non-peptide linear molecules linked through a non-amido linkage to form a peptide or pseudopeptide backbone, wherein one of the segments contains at least one non-coded structural unit and the non-coded structural unit does not form a part of the non-amido linkage, provided that both segments are not a non-peptide linear molecule at the same time.

This invention further provides a modified protein represented by the formula:

R-L-R' wherein R and R' are the same or different and are each a residue of a peptide or pseudopeptide; and L represents a thiol ester or selenol ester linkage. Preferably, both R and R' comprise from about two to about one hundred amino acid residues.

The above objects and features of the invention will become more fully apparent from the description of the preferred embodiments in conjunction with the accompanying figures.

DESCRIPTION OF THE PREFERRED EMBODIMENTS

Figure 1:
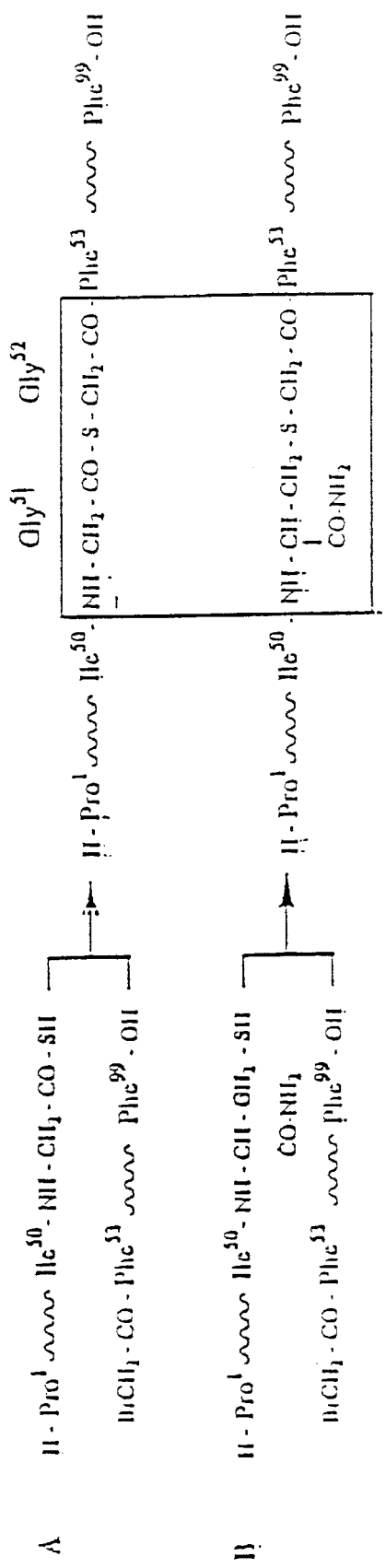
FIG. 1 shows a synthetic strategy for the total chemical synthesis of HIV-1 PR analogs in accordance with this invention where "A" schematically represents the coupling of the N-terminal segment HIV-1 PR (1–50, $Gly^{51}$ SH) and the C-terminal segment bromoacetyl (53–99) HIV-1 PR, and "B" schematically represents the coupling of the N-terminal segment HIV-1 PR (1–50, $Cys^{51}$amide) and the same C-terminal segment.

This invention is based on a conceptually novel approach to synthesizing large biomolecules such as proteins by a convergent type synthesis. Thus, when applied to the synthesis of modified proteins, this invention involves the coupling of at least two peptide segments to create a linkage which can be a non-amido bond. The peptide segments may be synthesized using solid phase peptide synthesis, solution phase synthesis, or by other techniques known in the art including combinations of the foregoing methods.

The present process involves the steps of:

a. providing a first segment having at least one non-coded structural unit, and a first chemoselective synthon at the terminal position thereof;

b. providing a second segment optionally containing at least one non-coded structural unit, and a second chemoselective synthon at the terminal position thereof, the second chemoselective synthon being complementary to the first chemoselective synthon of the first segment; and c. ligating the first segment and the second segment, whereby the first synthon of the first segment and the second synthon of the second segment forms a non-peptide linkage, wherein the first segment and the second segment are each selected from peptides, pseudopeptides, or non-peptide linear molecules, provided that both segments are not non-peptide linear molecules at the same time.

Preferably, both of the first and second segments are peptides or pseudopeptides having from about two to about one hundred amino acid residues. More preferably, the segments constitute from about forty to sixty amino acid residues.

Preferably, the non-peptide linkage formed is represented by one of the following linking moieties:

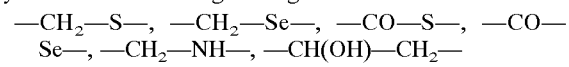

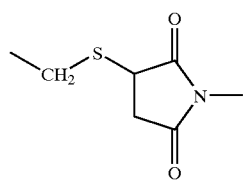

-continued

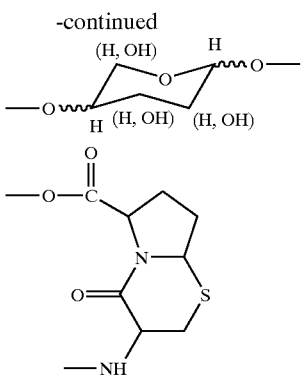

The present process allows at least two different non-coded structural units to be incorporated to the segments as well as allowing the same non-coded structural units to be incorporated at two sites.

In view of the broad and varied class of modified proteins which may be bound by this invention, all chemically modified proteins having such characteristics as defined above are deemed to be within the scope of this invention. However, for purposes of illustrative clarity and ease of comprehension, this invention will be described herein in more detail utilizing a modified HIV-1 protease as an embodiment. It should be understood that the use of this particular enzyme for descriptive purposes shall not restrict nor limit the use of other proteins or peptides.

As employed herein, the term "modified protein" is intended to include oligopeptides, oligopseudopeptides, polypeptides, pseudopolypeptides, and modified native proteins-synthetic or otherwise derived. The term "pseudopeptide" means a peptide where one or more peptide bonds are replaced by non-amido bonds such as ester or one or more amino acids are replaced by amino acid analogs. The term "peptides" refers not only to those comprised of all natural amino acids, but also to those which contain unnatural amino acids or other non-coded structural units. The terms "peptides", when used alone, include pseudopeptides. The "modified proteins" have utility in many biomedical applications because of increased stability toward in vivo degradation, superior pharmacokinetics, and enhanced or diminished immunogenecity compared to their native counterparts.

HIV-1 protease (HIV-1 PR) is a virally-encoded enzyme which cuts polypeptide chains with high specificity and which is essential for the replication of active virions (N. E. Kohl, et al., *Proc. Natl. Acad. Sci., U.S.A.*, 85:4686, 1988). The 21,500 dalton HIV-PR molecule is made up of two identical 99 amino acid polypeptide chains.

Comparison of the crystal structures of the empty (A. Wlodawer, et al., *Science*, 245:616, 1989) and inhibitor-bound (for example, M. Miller, et al., *Science*, 246:1149, 1989) enzyme revealed that on binding a substrate-derived inhibitor the HIV-1 molecule undergoes significant conformational changes which are particularly pronounced in two exterior, functionally-important "flap" regions. From these cystallography studies it appears that peptide bonds in the flap regions of the HIV-1 PR polypeptide backbone are involved in the formation of β-sheet/β-turn structure, in the interaction which occurs between the two subunits of the active dimer at the tip of each flap in the enzyme-inhibitor (substrate), complex, and in hydrogen bonding interactions with bound peptide inhibitors (and, presumably, substrates). Mutagenesis studies carried out with recombinant HIV-1 PR showed that the flap region is highly sensitive to changes in the amino acid sequence (D. D. Loeb, et al., *Nature*, 340:397, 1989).

These observations make the flap region especially interesting as a target for protein backbone modifications to investigate the role of peptide bond interactions in HIV-1 protease activity.

In the case of HIV-1 PR where modifications of the flap region are desired, this invention allows pseudo-peptide bonds to be introduced into the region. The $Gly^{51}$-$Gly^{52}$ bond of HIV-1 PR is particularly preferred for bond manipulation for two reasons. First, glycine is the only achiral amino acid and therefore there is no concern about loss of optical purity; and second, the $Gly^{51}$-$Gly^{52}$ bond is located near the middle of the 99 amino acid HIV-1 PR monomer polypeptide chain. This means that the two peptide segments which are to be coupled are each about 50 residues in length.

The solid phase peptide synthesis method is generally described in the following references: Merrifield, *J. Am. Chem. Soc.*, 888:2149, 1963; Barany and Merrifield, *In the Peptides*, E. Gross and J. Meinenhofer, Eds., Academic Press, New York, 3:285 (1980); S. B. H. Kent. *Annu. Rev. Biochem.*, 57:957 (1988). By the solid phase peptide synthesis method, a peptide of a desired length and sequence can be produced through the stepwise addition of amino acids to a growing peptide chain which is covalently bound to a solid resin particle. Automated synthesis may be employed in this method.

Accordingly, these embodiments can be accomplished by the steps of:

1. sequentially coupling amino acids to a terminal amino acid bound to a resin support to form a peptide segment-resin; and 2. cleaving the peptide segment from the resin support.

In the preferred application of this method, the C-terminal end of the growing peptide chain is covalently bound to a —$OCH_2$ PAM resin and amino acids having protected α-amino groups are added in the stepwise manner indicated above. A preferred α-amino protecting group is the tert-butyloxycarbonyl (BOC) group, which is stable to the condensation conditions and yet is readily removable without destruction of the peptide bonds or racemization of chiral centers in the peptide chain. At the end of the procedure the product peptide is cleaved from the resin, and any remaining protecting groups are removed by treatment under acidic conditions such as, for example, with a mixture of hydrobromic acid and trifluoroacetic acid, with trifluoromethane sulfonic acid or with liquified hydrogen fluoride.

In the case of HIV-1 protease, the C-terminal segment comprises the following amino acid sequence: $F^{53}IKVRQYD^{60}QIPVEICGHK^{70}AIG$ TVLV $GPT^{80}PVNIIGRNLL^{90}TQIGC$ $TLNF^{99}$ (SEQ. ID NO.1). The N-terminal segment comprises the following amino acid sequence: $P^1QITLWQRPL^{10}VTIRIGGQLK^{20}EALLDTGADD^{30}T$ $VLEEMNLPG^{42}KWK$ $PKMIGGI^{50}G^{51}$ (SEQ. ID NO.2). The synthesis of these segments normally require about 15 hours at a standard cycle speed.

If desired, any amino acids in the above sequences can be replaced by amino acid analogs or amino acid mimetic compounds known in the art. Suitable amino acid substitutes include β-alanine, L-α-aminoisobutyric acid, L-α-amino-n-butyric acid (Aba), 3,4dehydroproline, homoarginine, homocysteine, homoproline, homoserine, 3-mercaptopropionic acid, norleucine (Nle), penicillamine, pyroglutamic acid and sarcosine.

L-amino acids and D-amino acids may be used in this invention, particularly, D-amino acids are useful for the formation of a "reversible peptide sequence".

The "reversed" or "retro" peptide sequence as discussed above refers to that part of an overall sequence of covalently-bonded amino acid residues (or analogs or mimetics thereof) wherein the normal carboxyl-to-amino direction of peptide bond formation in the amino acid backbone has been reversed such that, reading in the conventional left-to-right direction, the amino portion of the peptide bond precedes (rather than follows) the carbonyl portion (see, generally, Goodman, M. and M Chorev, *Accounts of Chem. Res.*, 12:423, 1979).

The "reversed" peptides are within the meaning of the "peptides" used throughout the specification. D-amino acids, amino acid analogs and amino acid mimetic compounds are collectively referred to herein as "non-coded amino acids." Although the solid phase peptide synthesis theoretically enables one skilled in the art to prepare a peptide backbone of any length, the efficiency of coupling amino acids (addition of an amino acid in successive cycles) would necessarily limit the use of this technique when a peptide to be synthesized has greater than 150 residues. Preferably, for practical and economic reasons, the process of this invention employs from about two to about one hundred cycles.

Accordingly, the modified proteins obtained by the process of this invention have the general structure set forth in formula (1) and R and R' are as previously defined. If a larger peptide segment (containing greater than one hundred amino acid residues) is desired, such peptide segment may be available from naturally occurring proteins (native proteins) by enzymic or chemical degradation. Alternatively, the present process can be repeated with different ligation modes for building such large peptide segments.

An important feature of this invention is the bond formation linking two peptide segments (namely R and R' ). A variety of bond forming reactions can be used to covalently link the two peptide segments. Representative combinations of such groups are carbonylthiol with halo to form a thiol ester bond between the two segments, carbony selenol with melo to form a seleno ester, or thiol with thiol to form a disulfide bond, thiol with halo to form a thioether bond, selenol with halo to form a selenol ether, amino with isothiocyanate to form a thiourea bond, amino with aldehyde to form a imine bond which can be reduced to a carbon-nitrogen bond, thiol with maleimide to form a thioether bond, and gem-diol with boron to form oxygen-boron bonds, and hydroxyl with carboxyl to form an ester bond. Among these, preferred linkages are those already enumerated by way of their structure. A preferred linkage is a sulfur-containing or selenium-containing linkage which does not readily hydrolyze in vivo or which is more liable than an amido bond in vivo.

The most preferred linkage L is a thiol ester linkage. This linkage can be accomplished by first attaching a facile leaving group to a first peptide segment and by attaching carbonylthiol functionality to a second peptide segment followed by nucleophilic substitution where the sulfur nucleophile attacks the leaving group. Preferably, a haloacyl (e.g., haloacetyl) such as iodo, chloro, or bromoacetyl is attached to the N-terminus of the first peptide segment. The suitable haloacyl group may be straight or branched (substituted by alkyl). This step is conveniently carried out while the first peptide segment is still bound to a resin support.

To introduce a bromoacetyl group to the first peptide segment, suitable activated forms of bromoacetic acid may be employed in this invention. The particularly preferred agent for this purpose is bromoacetic anhydride.

When the aforementioned C-terminal segment of HIV-1 PR is derivatized with the N-bromoacetylating agent, the unprotected N-terminus of the protected peptide segment on resin is condensed with bromoacetic anhydride to produce bromoacetyl (53–99) HIV-1 PR. Deprotection and release of the product peptide segment from the resin support can be accomplished by standard conditions (e.g., treatment with anhydrous HF containing 10% p-cresol at 0° C. for several hours). The product peptide segment is precipitated, dried by lyophilization, and purified, if desired, by reverse phase HPLC, according to standard techniques known in the art.

To introduce carbonylthiol functionality to the second peptide segment, its terminal carboxylic acid moiety may be converted to a carbonylthiol group.

When the aforementioned N-terminal segment of HIV-1 PR is to be derivatized accordingly, 4-[α-(Boc-Gly-S) benzyl] phenoxyacetamidomethyl-resin is used as the resin support. If any amino acid or amino acid analog other than glycine is desired, that amino acid can be loaded on an aminomethyl-resin in the form of 4-[α-(Boc-X-S) benzyl] phenoxyacetic acid wherein X represents the amino acid.

The N-terminal derivatized peptide segment can thus readily be prepared by the stepwise solid phase synthesis. The second product peptide segment is cleaved from the resin support, deprotected, and isolated in the manner described above.

The thiol ester linkage can be generated by coupling the two segments under normal ligation conditions. The formation of the thiol ester linkage is highly chemoselective and thus compatible with most reactive groups that may be present in the molecules.

A typical ligation reaction is carried out by mixing the unprotected N—and C-terminal segments in 6M guanidine hydrochloride buffer at about pH, 3–6. In this buffer, the solubility of the unprotected peptide segments is very high, thus eliminating the major drawback of the prior art techniques having to use protected peptide fragments despite their limited solubility in ligation media. Other denaturants such as urea, detergents, and sodium dodecyl sulfate can be used as the ligation buffer.

The coupling of HIV-1 PR (1–50, Gly-SH) with bromoacetyl (53–99) HIV-1 PR is complete in several hours. The product peptide $[(NH\,CH_2COSCH_2CO)^{51-52}]$ HIV-1 PR can be isolated, purified and characterized by standard techniques.

When one of the peptide segments has any reactive groups which may interfere with the thiol ester formation, those groups may be protected by suitable protecting groups known in the art or the amino acids bearing such groups can be substituted by other amino acids or amino acid analogs which are reaction inert and yet do not adversely affect the biological activity of a product protein.

For example, in the Examples, the C-terminal segment of HIV-1 PR has two cysteine residues at positions 67 and 95. These cysteine positions have been shown to be replaceable by L-α-amino-n-butyric acid (Aba) without causing the loss of the enzymic activity of the native protease. In one embodiment of this invention, bromoacetyl $[(53–99)Aba^{57,95}]$ HIV-1 PR is used. Alternatively, to block a thiol group of the cysteine residues before the coupling reaction, the use of protecting groups that are compatible with ligation conditions are preferred. However, these precautions may not be necessary since, in present experience, the thiol ester group of the N-terminal segment attacks a bromoacetyl group even at low pH conditions where a thiol side chain of a cysteine residue is unreactive.

In another embodiment of the invention, the linkage L can be a thioether bond. This linkage can be accomplished in substantially the same manner as that described for the formation of the thiol ester linkage, except that thiol functionality is attached to a second peptide segment. This is conveniently accomplished by utilizing a thiol side chain of a cysteine residue. Thus, cysteine can be employed as the C-terminal amino acid of the second peptide segment (N-terminal segment). HIV-1 PR(1–50, $Cys^{51}$ amide) described herein represents one example of such derivatized second peptide segment where the cysteine's carboxylic acid is blocked as amide. When this peptide segment is subjected to the ligation conditions described earlier in the presence of bromoacetyl (53–99) HIV-1 PR, the coupling of the two peptide segments takes place rapidly to afford {[NHCH $(CONH_2)CH_2SCH_2CO]^{51-52}$}HIV-1 PR. The ligated produce protein can be isolated, purified, and characterized by standard techniques. In a further embodiment of the invention, the linkage can be a selenium-containing bond such as selenol ester and seleno ether. In like manner, a selenocysteine can be used in place of cysteine.

The process of this invention is applicable to the synthesis of any biomolecules and is not limited to proteins insofar as two constituent fragments are available by chemical synthesis or other biosynthetic methods. In particular, the present process: (1) allows rapid synthesis of modified proteins;(2) avoids the use of protecting groups in at least the critical bond formation stage;and (3) incorporates into the protein backbone structural units such as D-amino acids and amino acid analogs.

This invention will be described in further detail below by way of the aforeindicated embodiments, but these embodiments should not be taken as limiting the scope of the invention.

EXAMPLE 1

SYNTHESIS OF [$NHCH_2COSCH_2CO)^{51-51}Aba^{67,95}$] HIV-1 PR

Two peptide segments, HIV-1 PR (1–50, $Gly^{51}SH$) (PREPARATION 1) and bromoacetyl (53–99) HIV-1 PR (PREPARATION 2) were coupled by ligating the segments in 6M guanidine hydrochloride 0.1 M sodium phosphate at pH 4.3. The segments were separately dissolved in ligation buffer at a concentration of 20 mg/ml.

Figure 2:
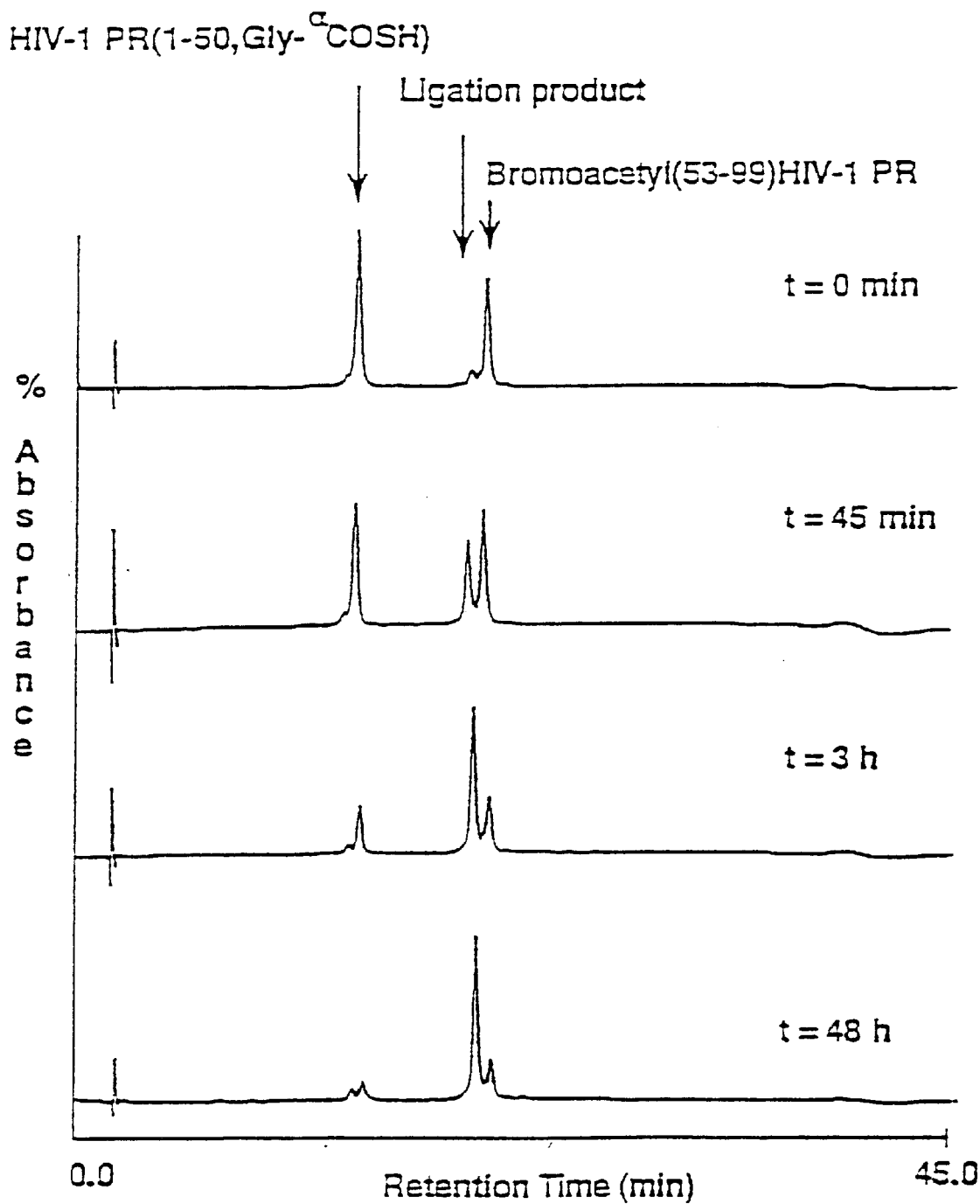
FIG. 2 shows an elution profile of aliquots taken at t=0, 45 min., 3 h, and 48 h from the ligation mixtures containing HIV-1 PR (1–50, $Gly^{51}$SH) and bromoacetyl (5399) HIV-1 PR by the practice this invention using reverse phase HPLC (absorbance 214 nm).

The process of the ligation was followed by reverse phase HPLC on a Vydac $C_{18}$ column using a linear gradient of 30–60% buffer B (90% acetonitrile/0.09% trifluoroacetic acid) in buffer A (0.1% trifluoroacetic acid) in 30 min. The flow rate was 1 ml/min and absorbance was monitored at 214 nm. Results are shown in FIG. 2.

Figure 3:
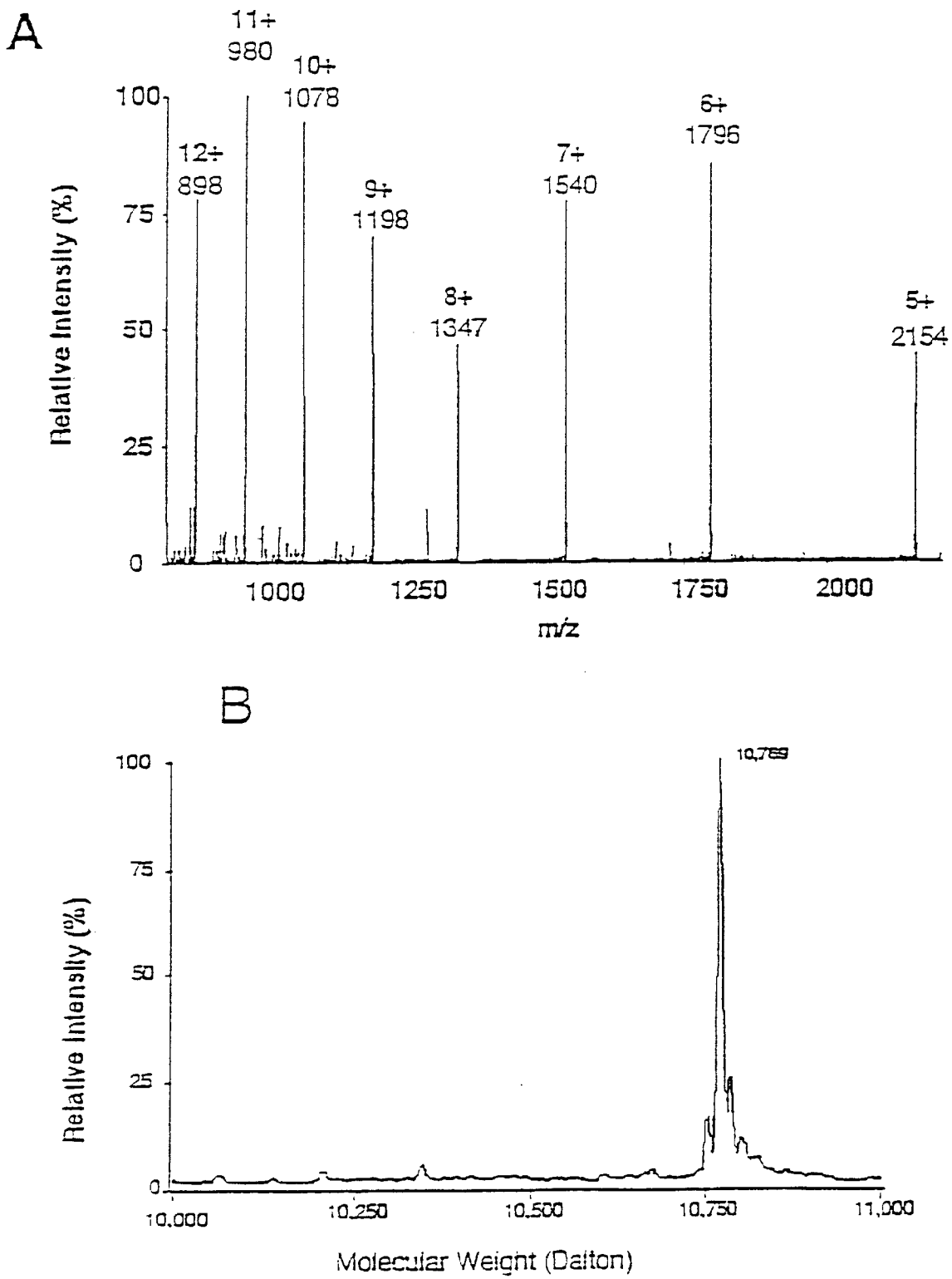
FIG. 3A shows the ion spray mass spectrum of the purified ($[NHCH_2COSCH_2CO]^{51-52}Aba^{57,95}$) HIV-1 PR where the labeled peaks represent a single molecular species differing in the number of excess protons.
FIG. 3B shows the deconvoluted mass spectrum of the purified ($[NHCH_2COSCH_2CO]^{51-52}Aba^{62,95}$) HIV-1 PR where the peak of the molecular weight of the enzyme is located at 10, 769 dalton.
Figure 4:
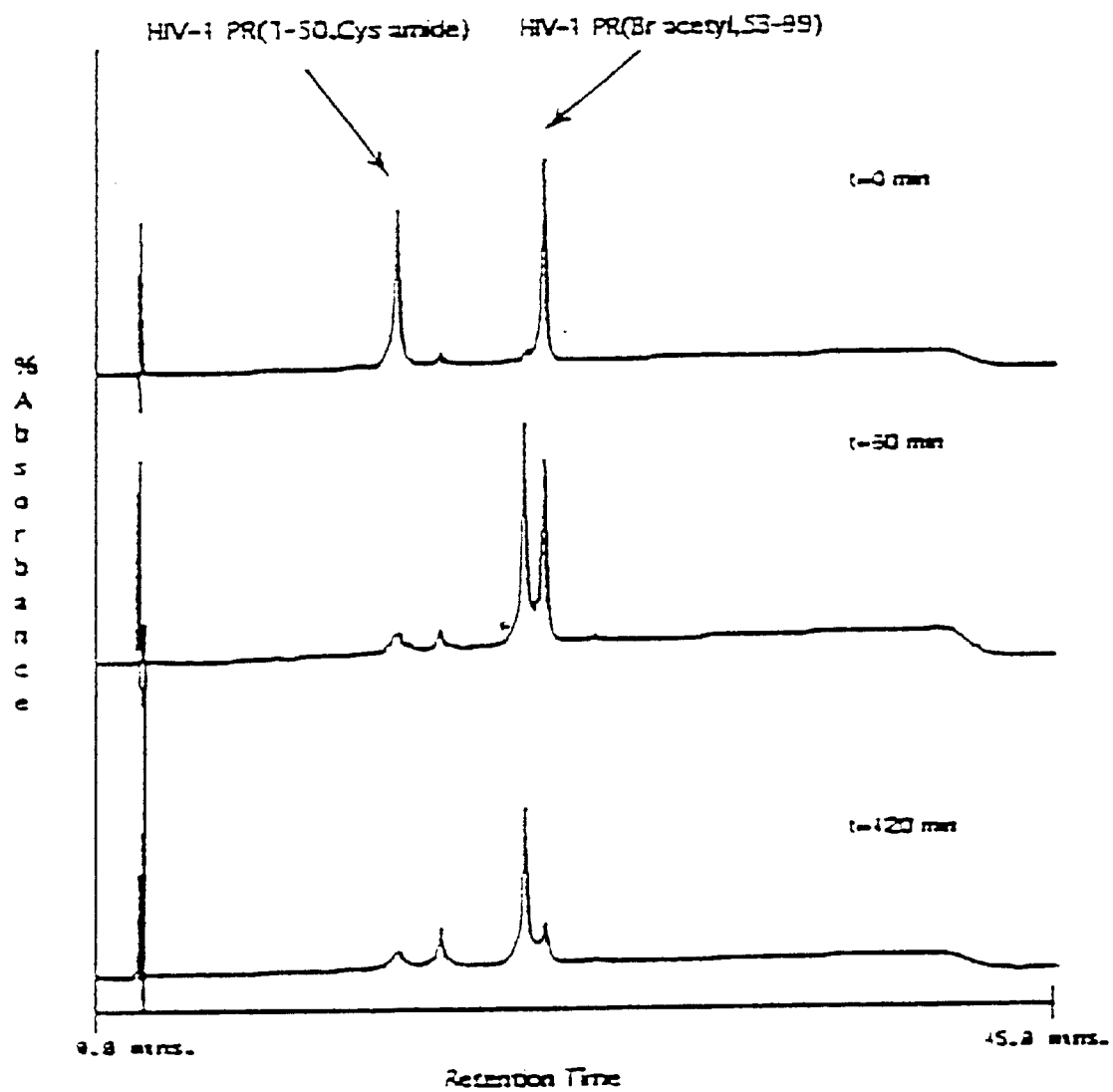
FIG. 4 shows an elution profile of aliquots taken at t=0, 30 min, and 120 min from the ligation mixture containing HIV-1 PR(1–50, Cys amide) and bromoacetyl (53–99)] HIV-1 PR.

The resulting ligated peptide was purified by reverse phase HPLC on a semipreparative Vydac $C_{18}$ column using various linear gradients of 90% acetonitrile/0.09% TFA in 0.1% aq TFA. The purity of the product peptide was checked by analytic HPLC as well as by ion spray mass spectrometry. The product peptide had the expected molecular weight of 10,768.6±1.1 Da (Calcd. for monoisotopic; 10,763.9 Da; (average) 10,770.8 Da). The mass spectra of the title peptide are shown in FIGS. 3A and 3B.

EXAMPLE 2

SYNTHESIS OF [(NHCH(CO $NH_2)CH_2 5CH_2CO]^{51-52}Aba^{67,95}$] HIV-1 PR

Two peptide segments HIV-1 PR (1–50, $Cys^{51}$ amide) (PREPARATION 1) and bromoacetyl (53–99) HIV-1 PR (PREPARATION 3) were coupled substantially according to the procedure of EXAMPLE 1, except that the pH was over 7.0. The ligation reaction was monitored by HCLP, with the results shown in FIG. 3. After work-up and purification, the product peptide had the expected molecular weight of 10,800.31±0.75 Da (Calcd. for monoisotopic 10,792.9 Da; (average) 10,799.8 Da).

EXAMPLE 3

ENZYMATIC ACTIVITY OF [$(NHCH_2COSCH_2CO)^{51-52}Aba^{67,95}$] HIV-1 PR

Figure 5:
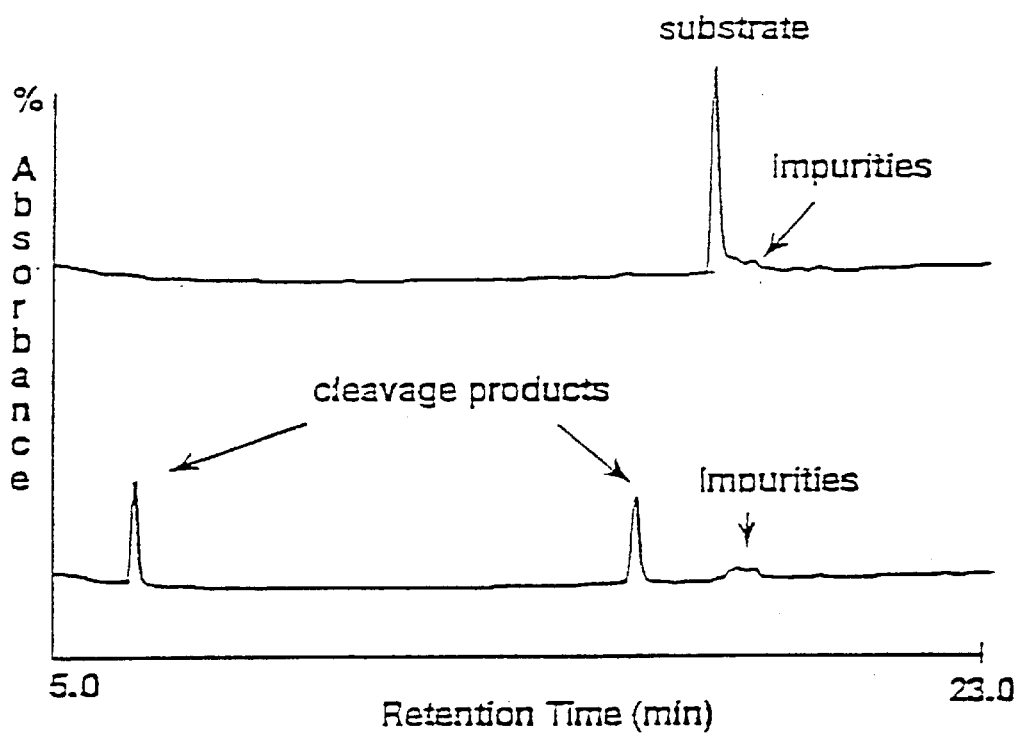
FIG. 5 shows an elution profile of the hexapeptide Ac-Thr-Ile-Nle-Nle-Gln-Arg; $NH_2$ before and after treatment with the ligation mixture taken at t=3h as shown in FIG. 2 using reverse phase HPLC with absorbance monitored at 214 nm, where the upper panel shows peaks before the treatment and the lower panel, peaks after the treatment, respectively.

An aliquot of the ligation reaction mixture after 3 hours ligation (EXAMPLE 1) was treated with a peptide substrate (1 mg/ml) having the sequence of Ac-Thr-Ile-Nle-Nle-Gln-Arg. $NH_2$ (SEQ. ID NO.3) (Nle:L-norleucine) at pH 6.5. Reaction was monitored by reverse phase HPLC using a Vydac C18 column with the results shown in FIG. 5. In FIG. 5 the upper panel shows the peptide substrate peaks before treatment. The lower panel shows the peaks of cleavage products after 15 min. treatment.

The cleavage produces were separated by reverse phase HPLC (Vydac $C_{18}$ column, linear gradient of 0–40% buffer B (90% acetonitrile/0.09% trifluoroacetic acid) in buffer A (0.1% trifluoroacetic acid) over 20 min, flow rate, 1 ml/min; absorbance monitored at 214 nm). The peptide products were identified by ion spray mass spectrometry as (H)-Nle-Gln-Arg. $NH_2$ (early eluting) and Ac-Thr-Ile-Nle-(OH) (late eluting).

Thus, the title peptide shows substantially the same specificity as the native enzyme HIV-1 PR against the substrate peptide employed in this assay.

Figure 6:
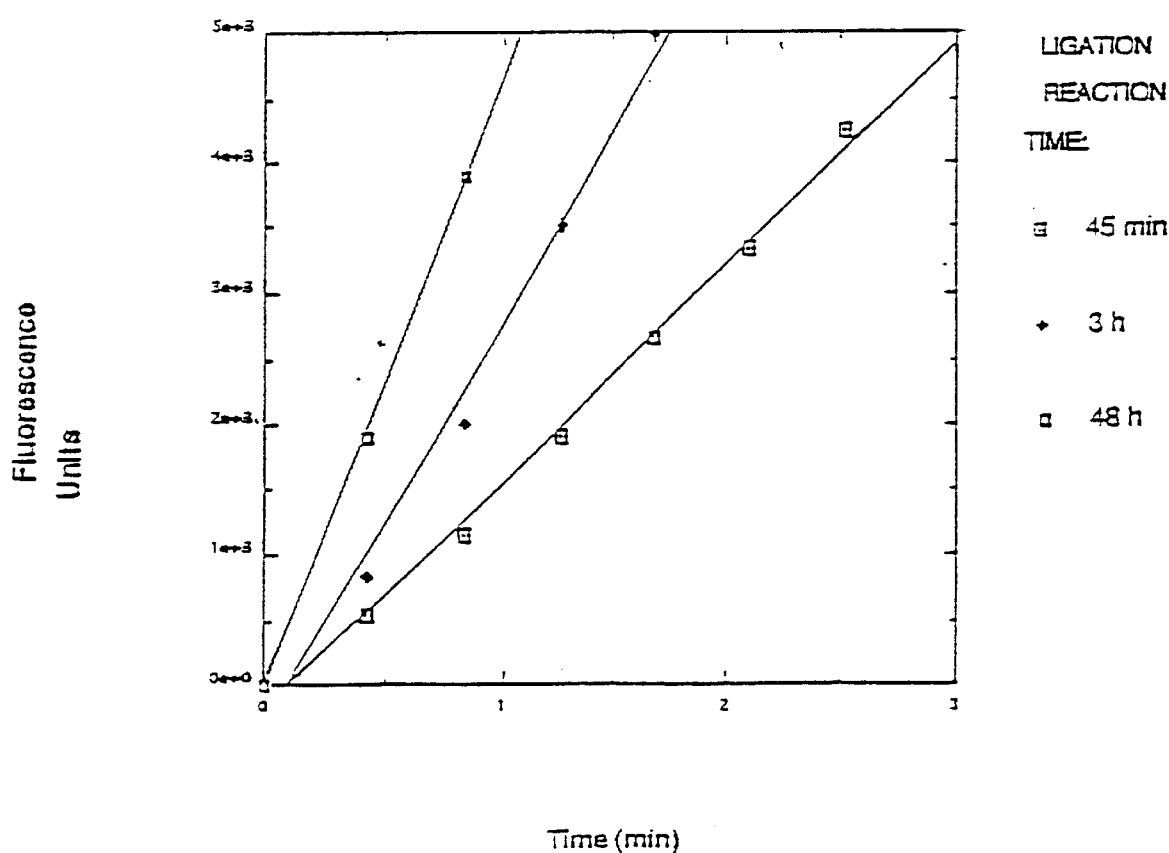
FIG. 6 shows a fluorogenic assay of aliquots of the ligation mixture taken at the times indicated as shown in FIG. 2 where data points illustrating fluorescence units were read from continuous chart recorder tracings.

Further, an aliquot of the ligation reaction mixture was treated with a solution containing a fluorogenic substrate in 100 mM MES buffer at pH 6.5. The fluorogenic substrate used was 2-aminobenzoyl-Thr-Ile-Nle- Phe(p-$NO_2$)-Gln-Arg-NH2 (SEQ. ID NO.4). Fluorescence was recorded as time of incubation. Date points shown in FIG. 6B were read from continuous chart recorder tracings. Quantitative comparison of ({NHCH $NH_2COSCH_2CO$}$^{51-52}Aba^{67,95}$) HIV-1 PR with an equal amount of {$Aba^{67,95,167,195}$} HIV-1 PR showed identical activities. Neither segment alone namely, HIV-1 PR(1–50, $Gly^{51}SH$), nor bromoacetyl (53–99; $Aba^{67,95}$) HIV-1 PR showed any activity (detection limit, <1 part in 1,000).

PREPARATION 1

HIV-1 PR (1–50, $Cys.^{51}$ Amide)

The synthesis of the title peptide was performed on an Applied Biosystem 430A peptide synthesizer. The instrument was modified by removal of delivery-line filters to, the top and bottom Reaction Vessel valve blocks, and the filter in delivery-line to the Cartridge needle. Larger (1.2 mm internal diameter) tubing was used from the DMF reservoir to the bottom reaction vessel valve block. A direct transfer line was used from the Activator (cartridge) valve block to the reaction vessel block (i.e., the Concentrator valve block was bypassed to allow direct transfer of the activated amino acid solution from the cartridge to the reaction vessel). Reagent positions 2 and 3 were connected to act -as a common reservoir for TFA, giving capacity of 900 ml (40+ cycles). The A-regulator pressure for TFA delivery was doubled to 5 psi for a delivery rate of 18 ml/min. Polypropylene bottle seals for the TFA bottles were replaced with Viton gaskets to prevent leaks The metering loop for reagent position 7 (DIEA for delivery to the Cartridge) was cut to length to deliver 0.72 g (5.60 mmol) DIEA. The metering loop for reagent position 8 (0.48 M HBTU in DMF) was cut to length to deliver 2.22 ml. Reagent position 1 was DIEA and was used only to deliver DIEA to fraction collector via the resin sampler. Reagent position 9 was DCM and was used to rinse residual DMF out of the cartridge prior to drying for reuse. Reagent position 10 was DMF. Positions 4, 5, and 6 were not used. A custom-designed 20 ml reaction vessel was used for all syntheses.

Synthetic cycles for use on the 430A were written from scratch. The Begin cycles only set toggle functions and rinsed the starting resin with DMF. The End cycle rinsed the product peptide-resin twice with DMF, then with DCM and dried the peptide-resin under nitrogen, special functions were written for the Concentrator and Activator programs, to allow the Activator program (i.e., events in the cartridge) to be coordinated with the Reaction Vessel program. These coordinating functions were similar in principle to the special function described by Reid and Simpson and the functions used in earlier rapid double couple cycles (Kent, et al., in "Peptides: Chemistry and Biology", *Process 10th Amer. Peptide Syn.*). A special function in the Activator program was also written to deliver Reagent 8 (0.48 MHBTU) to the cartridge. The synthetic protocols used are the following:

| Synthesis cycle | | Time/Mode |
| --- | --- | --- |
| Deprotect | 100% TFA | 2 × 30 sec flow wash 1 × 1 min, vortex |
| Wash | DMF | 1 × 1 min flow wash drain, minimize hold-up |
| Couple | activated Boc-AA* | 10 min, vortex |
| Wash | DMF | 1 × 30 sec flow wash take resin sample for ninhydrin test, drain |

*Activation of Boc-AA (scale: 0.2–0.5 mmol resin)
dissolve 2.25 mmol Boc-AA
in 4.44 ml 0.48 M HBTU (2.13 mmol) in DMF for 5 min
add 5.60 mmol DIEA
activate for 2.5 min
transfer from cartridge to reaction vessel The first TFA treatment consisted of 2×30 sec each upward vortexing flow washes followed by brief pulses of gas. After the batch treatment for 1 min, TFA was removed from the Reaction Vessel by a 1 min upward vortexing flow wash with DMF. The line from the resin sampler switching valve was rinsed into the Reaction Vessel with DMF in the middle of this DMF flow wash. The peptide-resin was drained by filtration under nitrogen pressure prior to the coupling step, in order to minimize the dilution of the activated Boc-amino acid. The activated Boc-amino acid solution was 0.25 M at transfer. Hold-up of DMF in the swollen peptide-resin reduced the concentration to about 0.15–0.2M in the reaction vessel. Brief DMF line rinses (0.3 ml each) were used to clean delivery lines after delivery of HBTU solution to the cartridge needle, and after the addition of the DIEA to the cartridge. The transfer line from the Activator valve block to the Reaction vessel was also rinsed with DMF before and after transfer of the activated Boc-amino acid solution. Peptide-resin samples (5–7 mg) were taken in DMF and stored in DIEA/DMF until analysis. Samples were washed thoroughly with DCM-MeOH (1:1 v/v) before drying and quantitative ninhydrin analysis. The overall cycle time for the addition of a single amino acid residue was 16 min 30 sec plus transfer times (Cartridge to Reaction Vessel, including rinses: ~2 min), plus the artefactual deadtime of 45 sec at the beginning of each cycle imposed by the operating software of the 430A. Total cycle time was 19 min 15 sec (about 75 residues per day).

The following chain protecting groups were used: D and E, cyclohexyl; N, xanthyl; Q and M, unprotected; K, 2-chlorobenzyloxycarbonyl (2CIZ); R, tosyl; Y, bromobenzyloxycarbonyl (BrZ); H, 2,4dinitrophenyl (DNP); T, benzyl. The formyl group was used to protect W(Trp). The peptide was removed from the resin by treatment with HF in the presence of 10% p-cresol for 1 hr at 0° C. $N_\alpha$-Boc group had been removed prior to the HF treatment 4-MeBHA-resin (4-methylbenzylhydrylamine) was used as the resin support in the above procedure.

The resulting peptide was precipitated with ether and finally dissolved in 50% acetic acid, diluted with water and lyophilized. Thus, starting with 216 mg of the resin, 1.36 g of the peptide resin resulted. The title peptide (181 mg) was obtained from 385 mg of the peptide resin.

The peptide was purified by reverse phase HPLC on a semipreparative Vydac $C_{18}$ column using various linear gradients of 90% acetonitrile/0.09% TFA in 0.1% aq TFA. This purity was checked by analytical HPLC as well as by ion spray mass spectrometry.

PREPARATION 2

BROMOACETYL [(53–99)Aba$^{57,95}$] HIV-1 PR

By employing the solid phase protein synthesis procedure as described in PREPARATION 1, the title peptide was prepared. Boc Phe (OCH$_2$)—phenylacetamidomethyl-resin (PAM resin) was used as the resin support. Thus, starting with 214 mg of the resin and through stepwise elaboration (46 cycles) of the peptide-resin was obtained. DNP and $N^\alpha$-Boc groups were removed prior to bromoacetylation. A protected peptide (Phe$^{53}$-Phe$^{99}$) was bromoacetylated using the conditions according to F. A. Robey, et al., *Ana. Biochem.*, 177:373, (1989).

To 525 mg protected peptide-resin 0.4 mmol bromoacetic anhydridl in 2 ml DCM/DMF (1:1 v/v) was added. The reaction was allowed to proceed as 25° C. for 30 min with shaking, after which time the reaction appeared to be complete as evidenced by the disappearance of free amine. The resin was filtered, washed with DMF, then DCM/T60W (50:50 v/v) and dried in vacuum. The peptide was removed from the resin by treatment with MF in the presence of 10% p-cresol for 1 hr at 0° C. The resulting peptide was precipitated with ether and finally dissolved in 50% acetic acid, diluted with water and lyophilized to produce 259 mg of the title peptide.

The peptide was purified by reverse phase HPLC on a semipreparative Vydac $C_{18}$ column using various linear gradients of 90% acetonitrile/0.09% TFA in 0.1% aq TFA. The purity was checked by analytical HPLC as well as by ion spray mass spectrometry. The purified sample had the molecular mass of 5235.8±0.2 daltons [Calc:(monoisotopic) 5231.8 daltons: (average) 5236.0 daltons].

PREPARATION 3

HIV-1 PR (1–50, Gly$^{51}$SH)

By employing the solid phase protein synthesis procedure as described in PREPARATION 1, the title peptide was prepared. 4-[α-(Boc-Gly-S) benzyl]-phenoxyacetamido methyl-resin was prepared as described by D. Yamashiro, et al., *Int. J. Peptide Protein Res.*, 31:322, (1988) and used as the resin support Starting with 359 mg 4-[α-(Boc-Gly-S) benzyl]-phenoxy acetamido methyl-resin and through stepwise elaborating (50 cycles) of the protected peptide chain, 1.1 g of the peptide-resin was obtained. In this synthesis, Gln, Trp, and Met were unprotected. The resulting peptide was precipitated with ether and finally dissolved in 50% acetic acid, diluted with water and lyophilized. The peptide was purified by reverse phase HPLC on a semipreparative Vydac $C_{18}$ column using various linear gradients of 90% acetonitrile/0.09% TFA in 0.1% aq TFA. This purity was checked by analytical HPLC as well as by ion spray mass spectrometry.

The invention now being fully described, it will be apparent to one of ordinary skill in the art that many changes and modifications can be made without departing from the spirit or scope of the invention.

What is claimed is:

1. A modified protein represented by the formula:

R-L-R' wherein

R and R' are the same or different and are each a residue of a peptide or pseudopeptide; and L represents a thiol ester pseudopeptide backbone linkage;

wherein both the peptide and pseudopeptide include from two to one hundred amino acid residues;

wherein the peptide or pseudopeptide of each R and R' includes a terminal residue;

wherein the thiol ester pseudopeptide backbone linkage L links the terminal residue of R with the terminal residue of R'; and wherein the thiol ester pseudopeptide backbone linkage is represented by $-CO-S-CH_2-CO-$;

with the following provisos:

R and R' each independently have a length of between 2 and 100 amino acid residues; and at least one of R and R' has a length of at least 50 amino acid residues.

2. The modified protein according to claim 1, wherein the protein is a protease.

3. The modified protein according to claim 1, wherein the peptide is a native peptide and the pseudopeptide is an analog of a native peptide.

4. A modified protein represented by the formula:

R-L-R' wherein

R and R' are the same or different and are each a residue of a peptide or pseudopeptide; and L represents a selenol ester pseudopeptide backbone linkage;

wherein both the peptide and pseudopeptide include from two to one hundred amino acid residues;

wherein the peptide or pseudopeptide of each R and R' includes a terminal residue; and wherein the selenol ester pseudopeptide backbone linkage L links the terminal residue of R with the terminal residue of R'.

5. The modified protein according to claim 4, wherein the protein is a protease.

6. The modified protein according to claim 4, wherein the selenol ester pseudopedtide backbone linkage is $-CO-Se-CH_2-CO-$.

7. The modified protein according to claim 4, wherein the peptide is a native peptide and the pseudopeptide is an analog of a native peptide.

* * * * *